(12) United States Patent
Tauber

(10) Patent No.: US 8,142,505 B2
(45) Date of Patent: Mar. 27, 2012

(54) INTERVERTEBRAL DISC REPLACEMENT

(75) Inventor: Michael Tauber, Haifa (IL)

(73) Assignee: Faneuil Innovations Investment Ltd.

( * ) Notice: Subject to any disclaimer, the term of this patent is extended or adjusted under 35 U.S.C. 154(b) by 347 days.

(21) Appl. No.: 12/278,414

(22) PCT Filed: Feb. 22, 2007

(86) PCT No.: PCT/IL2007/000239
§ 371 (c)(1),
(2), (4) Date: Aug. 6, 2008

(87) PCT Pub. No.: WO2007/096879
PCT Pub. Date: Aug. 30, 2007

(65) Prior Publication Data
US 2009/0062920 A1 Mar. 5, 2009

Related U.S. Application Data

(60) Provisional application No. 60/775,772, filed on Feb. 23, 2006.

(51) Int. Cl.
*A61F 2/44* (2006.01)
(52) U.S. Cl. ..................... 623/17.14; 606/247
(58) Field of Classification Search .... 623/17.11–17.16; 606/246–253
See application file for complete search history.

(56) References Cited

U.S. PATENT DOCUMENTS

| | | | |
|---|---|---|---|
| 698,789 A | 4/1902 | Bellows | |
| 5,425,773 A | 6/1995 | Boyd | |
| 5,562,738 A * | 10/1996 | Boyd et al. | 623/17.15 |
| 6,706,068 B2 | 3/2004 | Ferree | |
| 6,908,484 B2 | 6/2005 | Zubok et al. | |
| 6,972,037 B2 | 12/2005 | ZuZubok et al. | |
| 6,972,038 B2 | 12/2005 | ZuZubok et al. | |
| 6,981,989 B1 | 1/2006 | Fleischmann | |
| 6,986,789 B2 | 1/2006 | Schultz et al. | |
| 6,989,032 B2 | 1/2006 | Errico et al. | |
| 6,994,727 B2 | 2/2006 | Khandkar et al. | |
| 6,994,729 B2 | 2/2006 | Zubok et al. | |
| 6,997,955 B2 | 2/2006 | Zubok et al. | |
| 7,048,764 B2 | 5/2006 | Ferree | |
| 7,048,766 B2 | 5/2006 | Ferree et al. | |
| 7,083,649 B2 | 8/2006 | Zucherman et al. | |
| 7,291,173 B2 | 11/2007 | Richelsoph | |
| 7,758,646 B2 * | 7/2010 | Khandkar et al. | 623/17.15 |

(Continued)

FOREIGN PATENT DOCUMENTS

| | | |
|---|---|---|
| SG | 200805841-4 | 5/2009 |
| WO | WO2004/041131 | 5/2004 |
| WO | WO2004039285 | 5/2004 |

(Continued)

*Primary Examiner* — Thomas C. Barrett
*Assistant Examiner* — Melissa A Golob
(74) *Attorney, Agent, or Firm* — Mark M. Friedman

(57) ABSTRACT

An intervertebral disc replacement has two members attached to vertebral body endplates of two adjacent vertebrae. The two members are formed with respective articulation surfaces which form at least part of an articulation arrangement. When loaded with compressive axial force, the articulation arrangement supports the vertebral contact surfaces against the compressive force to ensure a predefined minimum intervertebral spacing, and allows a range of turning motion in all directions. The articulation arrangement is formed to provide an increase in the intervertebral spacing as a smooth function of angular displacement from a neutral position over at least part of the range of motion in each direction for each direction of motion, thereby providing motion attenuation and restoring forces.

20 Claims, 14 Drawing Sheets

U.S. PATENT DOCUMENTS

| | | | |
|---|---|---|---|
| 7,806,933 B2 * | 10/2010 | Sears et al. | 623/17.11 |
| 8,038,713 B2 | 10/2011 | Ferree | |
| 2004/0073311 A1 | 4/2004 | Ferree | |
| 2004/0225364 A1 | 11/2004 | Richelsoph et al. | |
| 2006/0116768 A1 * | 6/2006 | Krueger et al. | 623/17.14 |

FOREIGN PATENT DOCUMENTS

| | | |
|---|---|---|
| WO | WO 2004058098 | 7/2004 |
| WO | WO2006116851 | 11/2006 |
| WO | WO2007096879 | 8/2007 |
| WO | WO2008102333 | 8/2007 |

* cited by examiner

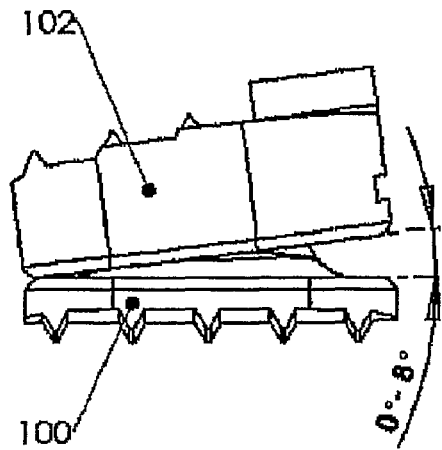
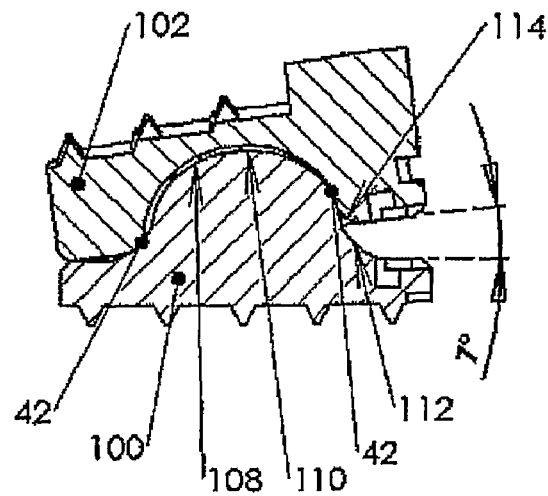
FIG. 4A        FIG. 4B
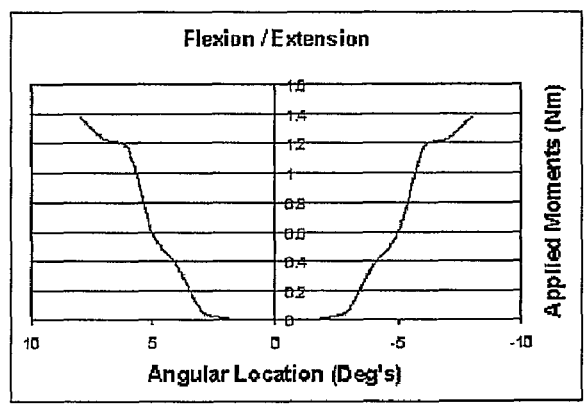
FIG. 4C
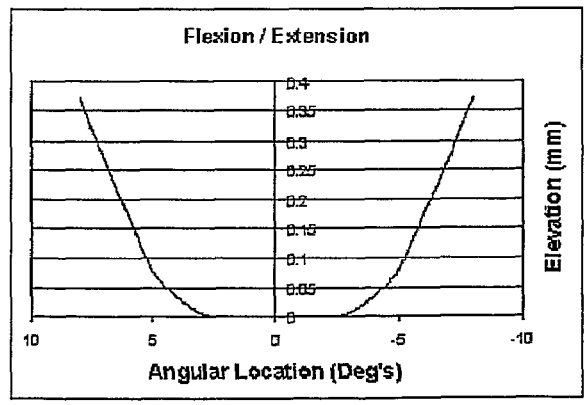
FIG. 4D

SECTION X-X

SECTION X-X

SECTION W-W

SECTION Z-Z

SECTION Y-Y

INTERVERTEBRAL DISC REPLACEMENT

FIELD AND BACKGROUND OF THE INVENTION

The present invention relates to intervertebral disc replacements and, in particular, it concerns an intervertebral disc replacement which allows motion about three rotational axes and provides motion attenuation to avoid end motion impact in motion about each of the axes.

Many commonly used Total Disc Replacements (TDR) are based upon a ball-and-socket type articulated joint. While a ball-and-socket is effective to provide a full range of motion in all directions, it does not provide motion attenuation. Specifically, with regard to axial rotation, the ball-and-socket joint itself inherently allows effectively unlimited rotation with minimal resistance. The vertebral section therefore relies upon surrounding soft tissue or impact of the facets to limit the motion, thus accelerating degeneration of the facets and the adjacent tissue. In anterior flexion, posterior extension and lateral bending, the motion is typically limited by impact of edges of the TDR flange upon each other, generating repeated impacts during normal use which may lead to degeneration of the TDR itself, or of the surrounding tissue.

More specifically, and to provide a reference for comparison with the present invention to be described below, FIGS. 11A-11C show cross-sectional views of a TDR based on ball-and-socket geometry in various positions of lateral bending, while FIGS. 11D and 11E show the bending moment and the elevation (corresponding to "intervertebral spacing", to be defined below) as a function of angular displacement from a central ("neutral") position. The normal range of motion of the joint is from the neutral position of FIG. 11A to the flange-on-flange contact position of FIG. 11B, here corresponding to a deflection of about 6 degrees. Within this range, as shown in FIG. 11D, minimal bending moment is required to generate motion, only needing to overcome any frictional resistance of the joint. Once contact occurs between the flanges, there is a sudden resistance to further deflection such that a gradually increasing applied moment does not generate any further motion. Only if the torque exceeds a certain threshold, deflection will continue by lifting the ball out of the socket as shown in FIG. 11C, a state which is not normally intended to occur. Once started, the lifting motion will continue at constant applied torque. The corresponding graph of intervertebral spacing as a function of angular deflection is shown in FIG. 11E. Within the normal ball-and-socket operating range of 0-6 degrees, no elevation occurs. If sufficient torque is then applied to start lifting the ball out of the socket, the intervertebral spacing starts to increase steeply, initially as an approximately linear function of deflection angle.

Various attempts have been made to develop an articulation arrangement for a TDR which more closely emulates various aspects of the dynamics of the natural intervertebral disc. These include a wide range of devices employing cylindrical bearings or saddle-like articulation surfaces. Examples of such devices may be found in the following U.S. Pat. Nos. 6,706,068; 6,908,484; 6,972,037; 6,972,038; 6,986,789; 6,989,032; 6,994,727; 6,994,729; 6,997,955; 7,048,764; and 7,048,766, and in the following US Patent Application Publication Nos.: 2004/0225364; and 2004/0073311.

Of particular interest as background to the present invention, some of the above-referenced documents introduce a concept of distraction (i.e., increased intervertebral spacing) as a function of angular displacement of axial rotation in order to generate restorative (self-centering) forces. Specifically, since the normal state of the spinal column is to be loaded axially with the weight of the upper body, an articulation arrangement which causes distraction of the joint as a function of axial rotation performs work against the loading, resulting in a restoring force which tends to return the joint to a neutral position of axial rotation. An example of such teachings may be found in the aforementioned U.S. Pat. No. 6,994,727.

Although the concept of joint distraction under applied load to provide a restoring force is discussed in the aforementioned document, it is only applied in a single mode of motion, namely, axial rotation. Furthermore, the documents currently known to the inventor do not provide any acceptable solution for motion attenuation in order to limit the range of motion for each type of motion without causing impact or otherwise endangering surrounding tissue.

There is therefore a need for an intervertebral disc replacement which would allow motion about three rotational axes and provide motion attenuation to avoid end motion impact in motion about each of the axes.

SUMMARY OF THE INVENTION

The present invention is an intervertebral disc replacement which allows motion about three rotational axes and provides motion attenuation to avoid end motion impact in motion about each of the axes.

According to the teachings of the present invention there is provided, an apparatus for replacing at least a portion of an intervertebral disc in a spinal column between endplates of a first vertebral body and a second vertebral body of a spinal column, the apparatus comprising: (a) a first member having a first vertebral contact surface for engagement with the first vertebral body endplate, and having a first articulation surface; and (b) a second member having a second vertebral contact surface for engagement with the second vertebral body endplate, and having a second articulation surface, wherein an intervertebral spacing is defined as the axial component of a line extending between a centroid of the first vertebral contact surface and a centroid of the second vertebral contact surface, and wherein the first articulation surface and the second articulation surface form at least part of an articulation arrangement configured such that, when loaded with compressive axial force: (i) the first and second vertebral contact surfaces are supported against the compressive force to ensure a predefined minimum intervertebral spacing; (ii) the second member is displaceable relative to the first member in motion corresponding to axial rotation, anterior-flexion and posterior extension, and lateral bending, each of the motions having a corresponding range of motion; and (iii) the intervertebral spacing increases as a smooth function of angular displacement from a neutral position over at least part of the range of motion in each direction for each of the axial rotation, anterior-flexion and posterior extension, and lateral flexion, thereby providing non-impact motion attenuation.

According to a further feature of the present invention, the articulation arrangement is configured such that a first derivative of intervertebral spacing as a function of angular displacement from a neutral position increases substantially monotonically with respect to the angular displacement from the neutral position over a majority of the range of motion for motion in each direction for each of the axial rotation, anterior-flexion and posterior extension, and lateral flexion.

According to a further feature of the present invention, the articulation arrangement is configured such that the second member is displaceable relative to the first member in motion corresponding to combinations of axial rotation, anterior flexion or posterior extension, and lateral bending.

According to a further feature of the present invention, the articulation arrangement is configured such that the apparatus is self-centering under axial loading so as to tend to return substantially to a predefined neutral position.

According to a further feature of the present invention, the first member and the second member are rigid bodies.

According to a further feature of the present invention, the first member and the second member are formed primarily from metallic material.

According to a further feature of the present invention, the first member and the second member are formed primarily from ceramic material.

According to a further feature of the present invention, the first articulation surface and the second articulation surface are deployed in direct contact to provide the articulation arrangement.

According to a further feature of the present invention, the first articulation surface features a protuberance and the second articulation surface features a cooperating recess, wherein the protuberance is shaped such that, in sagittal cross-section, an external shape of the protuberance features: (a) a convexly curved crown region having varying curvature with a local minimum of curvature at a crest of the crown region; and (b) a concavely curved transition region at the base of the protuberance.

According to a further feature of the present invention, the protuberance is further shaped such that, in coronal cross-section, an external shape of the protuberance features: (a) a convexly curved crown region having varying curvature with a local minimum of curvature at a crest of the crown region; and (b) a concavely curved transition region at the base of the protuberance.

According to a further feature of the present invention, the protuberance is further shaped such that a width of the protuberance in the coronal cross-section is greater than a width of the protuberance in the sagittal cross-section.

According to a further feature of the present invention, the protuberance is further shaped such that, in axial cross-section, an external shape of the protuberance is substantially elliptical.

According to a further feature of the present invention, the cooperating recess is formed substantially as an elliptical concavity with a convexly curved transition region connecting to a surrounding area of the second articulation surface.

According to a further feature of the present invention, the protuberance exhibits a plurality of recessed flank regions, and wherein the cooperating recess includes a corresponding plurality of ridge regions.

According to a further feature of the present invention, the first articulation surface features a protuberance including a plurality of ridges, and wherein the second articulation surface features a cooperating recess including a plurality of channels for receiving the ridges, wherein the ridges interact with adjacent surfaces of the channels to generate the increase in intervertebral spacing.

According to a further feature of the present invention, the first articulation surface features a plurality of protuberances and the second articulation surface features cooperating recessed features.

According to a further feature of the present invention, the first articulation surface features a plurality of recesses and the second articulation surface features a corresponding plurality of recesses, the articulating arrangement further including a corresponding plurality of bearing elements, each of the bearing elements being entrapped between a facing pair of the recesses of the first and second articulation surfaces.

According to a further feature of the present invention, the bearing elements are implemented as ball bearings.

According to a further feature of the present invention, the plurality of recesses of the first and second articulation surfaces are implemented as partial spherical recesses of radius of curvature greater than the ball bearings, locations of the recesses of the first articulation surface being offset relative to locations of the recesses of the second articulation surface.

According to a further feature of the present invention, the articulation arrangement is implemented with four of the ball bearings and four of the recesses in each of the first and second articulation surfaces.

BRIEF DESCRIPTION OF THE DRAWINGS

The invention is herein described, by way of example only, with reference to the accompanying drawings, wherein:

FIG. 4A is a lateral view of the intervertebral disc replacement of FIG. 1A undergoing posterior extension;

FIG. 4B is a sagittal cross-sectional view of the intervertebral disc replacement of FIG. 1A undergoing posterior extension;

FIG. 4C is a graph showing an applied moment of flexion or extension and the corresponding angular deflection of flexion or extension from a neutral position for the intervertebral disc replacement of FIG. 1A under conditions of axial loading;

FIG. 4D is a graph showing axial elevation (increase in intervertebral spacing) as a function of angular deflection of flexion or extension from a neutral position for the intervertebral disc replacement of FIG. 1;

DESCRIPTION OF THE PREFERRED EMBODIMENTS

Figure 1A:
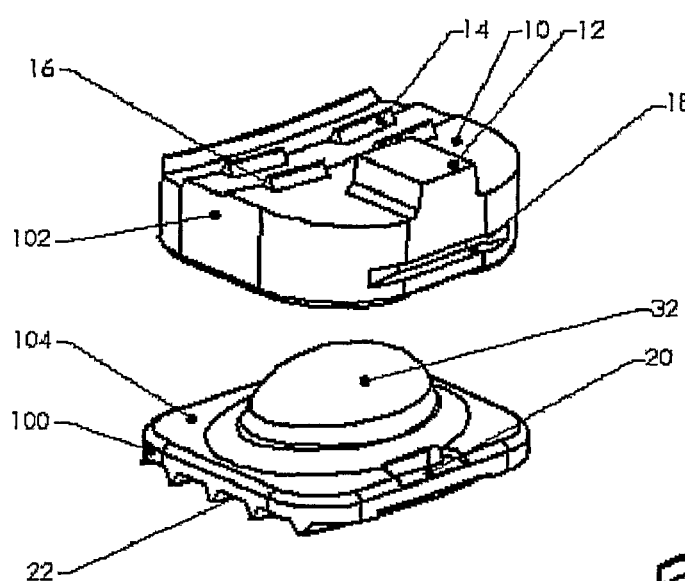
FIG. 1A is an isometric view of an intervertebral disc replacement, constructed and operative according to the teachings of the present invention, showing first and second members separated.

The present invention is an intervertebral disc replacement which allows motion about three rotational axes and provides motion attenuation to avoid end motion impact in motion about each of the axes.

The principles and operation of intervertebral disc replacements according to the present invention may be better understood with reference to the drawings and the accompanying description.

Referring now to the drawings, FIGS. 1A-5C illustrate a first preferred embodiment of an apparatus, constructed and operative according to the teachings of the present invention, for replacing at least a portion of an intervertebral disc in a spinal column between endplates of a first vertebral body and a second vertebral body of a spinal column.

In general terms, this and other embodiments of the apparatus have a first member 100 having a first vertebral contact surface 22 for engagement with the first vertebral body endplate, and a second member 102 having a second vertebral contact surface 10 for engagement with the second vertebral body endplate. First and second members 100 and 102 are formed with respective articulation surfaces 104 and 106 which form at least part of an articulation arrangement. The articulation arrangement is configured such that, when loaded with compressive axial force: (i) the first and second vertebral contact surfaces are supported against the compressive force to ensure a predefined minimum intervertebral spacing; (ii) the second member is displaceable relative to the first member in motion corresponding to axial rotation, anterior-flexion and posterior extension, and lateral bending, each of the motions having a corresponding range of motion; and (iii) the intervertebral spacing increases as a smooth function of angular displacement from a neutral position over at least part of the range of motion in each direction for each of the axial rotation, anterior-flexion and posterior extension, and lateral flexion, thereby providing non-impact motion attenuation.

Put in other words, the various embodiments of the present invention provide intervertebral disc replacements which provide support for axial loading, which allow a range of motion around three axes similar to the natural range of motion, and which generate progressive increase in intervertebral spacing for motion around each of the axes so as to achieve motion attenuation for all types of motion. A wide range of geometries may be employed in order to achieve the stated properties. By way of non-limiting examples, six particularly preferred embodiments will be presented herebelow.

At this stage, it will already be appreciated that the present invention offers a number of particular advantages compared to existing intervertebral disc replacements. In particular, by providing motion with mechanical attenuation in each direction of motion, a full range of motion similar to the natural range of motion is provided while avoiding problems of accelerated tissue degeneration due to the end-motion impact of the existing devices. This and other advantages will become clearer from the following description.

The desired magnitude of intervertebral spacing increase for a given deflection from the neutral position may be derived as follows. Energy conservation (disregarding friction) requires that:

$$\int M \cdot d\alpha = \int F \cdot dx$$

where:

M is the applied moment to generate the rotation about a given axis;

$\alpha$ is the angular deflection generated by the applied moment;

F is the axial loading force applied on the bearing device; and x is the increase in intervertebral spacing.

Thus, if a desired relation between applied moment and angular deflection is given as a predefined function $M = f(\alpha)$, and the applied load is assumed to be a predetermined constant weight F, the required increase in intervertebral spacing can be expressed as a function of angle as:

$$x = \frac{1}{F} \int f(\alpha) \cdot d\alpha$$

Figure 11A:
FIGS. 11A-11C, discussed above, are schematic coronal cross-sectional views taken through a conventional ball-and-socket joint in different stages of lateral bending.
Figure 11B:
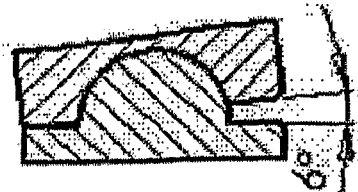
Figure 11C:
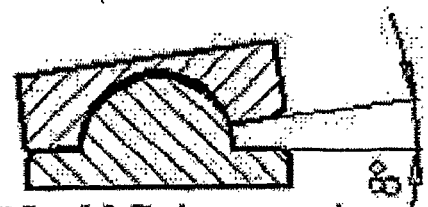
Figure 11D:
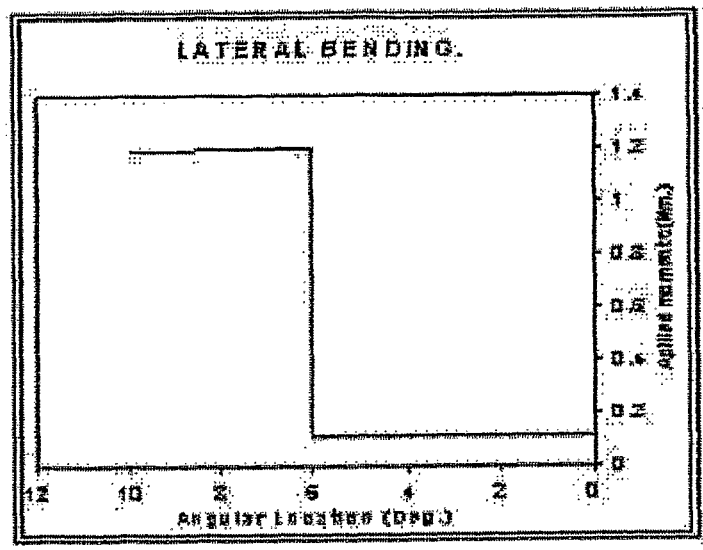
FIG. 11D is a graph showing an applied moment of lateral bending and the corresponding angular deflection of lateral bending from a neutral position for the ball-and-socket joint of FIG. 11A.
Figure 11E:
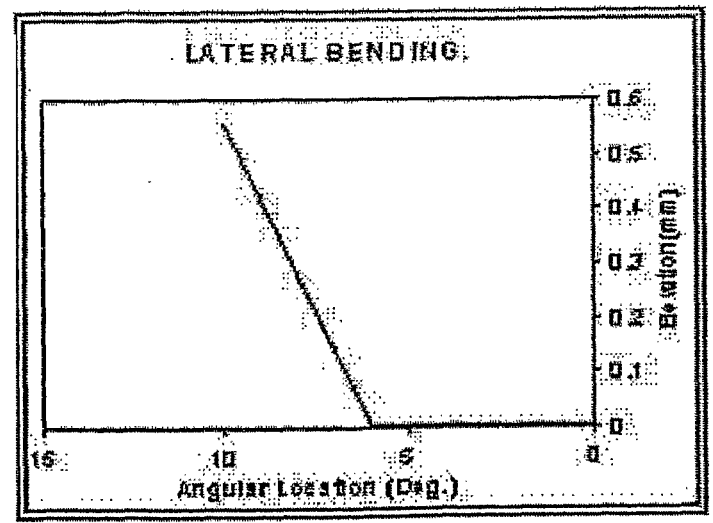
FIG. 11E is a graph showing the variation of axial elevation (increase in intervertebral spacing) as a function of angular deflection of lateral bending from a neutral position for the ball-and-socket joint of FIG. 11A.

This relation can be defined for each of the directions of motion. In order to avoid impact during motion, function $f(\alpha)$ is chosen to be a continuous function, i.e., where small changes in angle correspond to small changes in the required moment (also referred to herein as being "without any step"), thereby distinguishing the invention from the conventional ball-and-socket as represented in FIG. 11D. Most preferably, function $f(\alpha)$ is chosen to increase monotonically with increasing magnitude (in positive and negative directions) of angular deflection over at least the part of the range of motion in which motion attenuation is required. This ensures that the slope of intervertebral spacing as a function of angular deflection becomes increasingly steep as the magnitude of deflection increases, thereby providing particularly effective motion attenuation.

Once the desired relationship between intervertebral spacing and angle of deflection has been defined for each axis of motion, articulation surfaces are designed to provide the required motion. An additional consideration is that motion in each of the main directions should be combinable while maintaining non-impact motion attenuation properties. Additionally, care must be taken to ensure that the effective center of rotation (which may move during the motion) is compatible with vertebral kinematics, and in particular, that collision between vertebral facets is avoided. In the examples illustrated below, the center of curvature moves dynamically during motion in the lateral bending and flexion/extension directions, but preferably remains generally within the intervertebral space. Some small extent of linear displacement may also be accommodated to mimic the physiological behavior of the natural intervertebral disc, typically with a range of motion no greater than about 0.5 millimeter.

It should be noted that the required geometrical properties may be provided by a wide range of different articulation surface geometries which have the general property of increasing elevation as a function of angular deflection. A number of specific non-limiting examples of suitable articulation arrangements will be described below. Fine tuning of the design parameters for each type of geometry may be performed using computer aided design (CAD) tools to achieve the required elevation for each magnitude of deflection.

Before referring to further details of preferred implementations of the present invention, it will be useful to define certain terminology as used herein in the description and claims. Firstly, reference is made to a "neutral position" of the intervertebral disc replacement. This is a position taken to be the normal un-flexed state of the apparatus when implanted within a spinal column. In cases in which the articulation surfaces of the upper and lower members include substantially flat peripheral regions, the neutral position preferably corresponds to a substantially parallel state of the flat regions. In most preferred embodiments, the apparatus is self-biasing under axial loading so as to return towards the neutral position.

For the most part, the terminology used when describing the geometry of the apparatus of the present invention is the medical terminology, although this terminology may be used interchangeably with alternative mechanical terminology at times. The medical terminology is to be interpreted according to the context of the intended location and orientation in which the device is to be deployed in the body, although the terminology is used to refer to the device when standing alone. Thus, a central vertical plane passing front-to-back through the device is termed "sagittal" while a cross-ways vertical plane passing side-to-side is termed "coronal" and a horizontal plane is termed "axial". Similarly, a front view is termed "ventral", a rear view "dorsal", a side view "lateral" and a top view "axial".

Regarding types of motion, here too preference is given to the normal medical terminology for the corresponding body movements. Thus, bending forward is "(anterior) flexion", bending backwards is "(posterior) extension", bending sideways is "lateral bending", and twisting to the sides is "axial rotation". For convenience, reference is made to "axes" of deflection or rotation, which are side-to-side for flexion and extension, front-to-back for lateral bending and vertical for axial rotation. It should be noted, however, that these motions are typically not pure rotations about a fixed axis, but rather more complex motions in which the effective center of rotation shifts during the course of the motion.

It will also be noted that the motion referred to herein is always relative motion between the first and second members of the apparatus, corresponding to the motion superior and inferior vertebrae to which the respective members are fixed. For convenience, the motion may be referred to herein as if the lower member is fixed in a horizontal plane and the upper member moves. Clearly, when the apparatus is implanted in the body, the actual orientation of the members will be the local orientation of the relevant vertebral segment, with the apparatus working in cooperation with other vertebral segments (with either natural discs or additional apparatuses according to the present invention) to provide the overall total motion properties required of the spinal column.

When reference is made to "first" and "second" members, unless otherwise stated, it should be assumed that the features described may be applied interchangeably to the superior (upper) and inferior (lower) members. Notwithstanding this generality, in embodiments which have one element with one or more projection and the other with one or more recess, it is generally preferred that the recess is formed downward facing in the superior member so as to avoid accumulation of any mechanical debris which might find its way to the site.

Used in the context of vertebral bodies, the terms "first" and "second" are used herein in the description and claims as non-specific labels to refer to any pair of adjacent vertebral bodies between which the apparatus of the present invention is to be inserted. In fact, with suitable choice of dimensions and geometry, the present invention may be employed to advantage at one location or multiple locations throughout the cervical, thoracic and lumbar regions of the spinal column, from the joint of cervical vertebrae C2/C3 through to the bottom lumbar joint of L5/S1.

Reference is made herein to an "intervertebral spacing." This parameter is employed as a measure of the elevation occurring during motion of the apparatus. The rate of change of this elevation with angular deflection under axial loading corresponds to the restoring force biasing towards the neutral position, as will be described in more detail below. For pure axial rotation, where the upper and lower members remain roughly parallel, the variation in intervertebral spacing may be intuitively understood as the variation in distance between the vertebral contact surfaces. In flexion, extension and lateral bending, however, the intervertebral spacing must be more carefully defined since the tilting of one element relative to the other necessarily generates regions of the members which get closer and regions which get further away. The intervertebral spacing is therefore defined as the separation between the central regions of the two vertebral contact surfaces. In more precise terms, the parameter used may be defined as the axial component of a line extending between a centroid of the first vertebral contact surface and a centroid of the second vertebral contact surface. In this context, a "centroid" is taken as the center of mass of a thin flat sheet of uniform thickness having a common outline with the entire vertebral contact area, but neglecting vertical features such as the various fixation ridges and other surface features. The "axial component" is evaluated as the component parallel to the axis of pure axial rotation in the neutral position of the apparatus. For most applications, where the range of motion in each direction of deflection is in the single digits of degrees, the angles are sufficiently small that the difference between the definition given above and the simple distance between the centroids is not great.

The variation of the intervertebral spacing is described herein as a "smooth function" of angular displacement from the neutral position. The term "smooth function" is used herein to refer to any function which can be differentiated at all points within the relevant range. In other words, the variation of intervertebral spacing with angular displacement is "smooth" in that it does not have any abrupt changes in gradient. As a result, the restoring moment acting as a result of axial loading, corresponding to the derivative of the intervertebral spacing with respect to angle, does not have any sudden steps, and the motion attenuation is therefore non-impact attenuation.

Finally with regard to definitions, various features will be referred to as "recesses" or "projections". It should be noted that the term "recess" is used herein to refer to a surface which can be sealed by addition of a single plane to enclose a volume. A recess thus defined includes recesses which may have local projecting or convexly curved features within them, but excludes saddle-like forms. Conversely, a "projection" or "protuberance" from a surface is defined as a part of a body which could be severed from the underlying surface by cutting along a single plane, independent of whether the surface of the projection or protuberance includes localized recesses or concavely curved features.

Turning now to the features of the first embodiment in more detail, FIGS. 1A-5C illustrate a first embodiment in which first and second members 100 and 102 are formed with respective articulation surfaces 104 and 106 deployed in direct contact to provide the articulation arrangement. In this implementation, the geometry of the articulation surfaces is based upon modified elliptical profiles.

By way of introduction to this geometry, it will be noted that an ellipse lying on its "side", i.e., with its short axis perpendicular to and contacting an underlying surface, inherently has the property that its center of mass is raised by any angular tilting. The same is true for two perpendicular axes of tilting in the case of an oblate spheroid. As a result, the use of elliptical or near-elliptical geometry provides a good starting point for certain embodiments of the present invention.

In the first embodiment of the present invention shown here, the first articulation surface 104 features a protuberance 32 and the second articulation surface 106 features a cooperating recess 30. Protuberance 32 is shaped such that, in sagittal cross-section (FIG. 4B), an external shape of the protuberance features a convexly curved crown region 108 having varying curvature with a local minimum of curvature at a crest 110 of the crown region. This provides a function similar to the elliptical geometry mentioned above. Additionally, protuberance 32 is preferably formed with a concavely curved transition region 112 at the base of the protuberance. The flank surfaces of protuberance 32, i.e., where the convex region joins with the concave transition region preferably reaches a maximum inclination (steepness) relative to the underlying plane of articulation surface 104 which is less than 90 degrees, and typically in the range from about 60 to about 80 degrees.

Protuberance 32 is preferably further shaped such that, in coronal cross-section (FIG. 3B), an external shape of protuberance 32 similarly features a convexly curved crown region 108 having varying curvature with a local minimum of curvature at a crest 110 of the crown region, and a concavely curved transition region 112 at the base of the protuberance. As seen in the figures, a width of protuberance 32 in these two directions is different, with the width in the coronal cross-section preferably greater than the width in the sagittal cross-section.

In plan view of articulation surface 104, or in axial cross-section, protuberance 32 preferably has a substantially elliptical external shape. In other words, the aforementioned cross-sectional shapes in a sagittal and coronal plane are preferably joined smoothly through a substantially elliptical profile. The overall result is a rounded, but somewhat flat-topped, bulge which flairs outwards at its base, as best seen in FIG. 1A.

In the preferred case illustrated here, the cooperating recess 30 is formed substantially as an elliptical concavity, i.e., part of an ellipsoid, modified to provide a convexly curved transition region 114 connecting to a surrounding area of the second articulation surface 106.

Figure 1B:
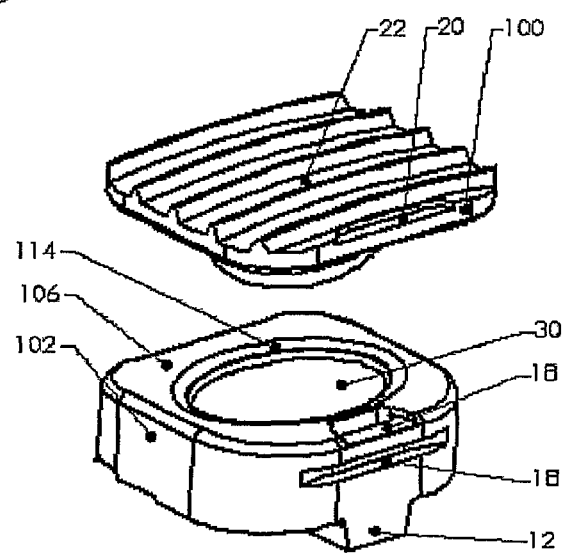
FIG. 1B is an inverted isometric view of the intervertebral disc replacement of FIG. 1A.
Figure 1C:
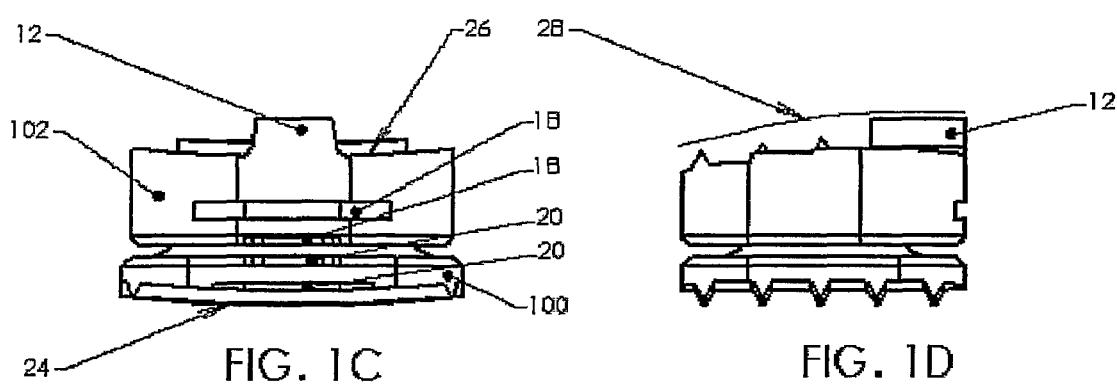
FIG. 1C is a dorsal view of the intervertebral disc replacement of FIG. 1A assembled.
Figure 1D:
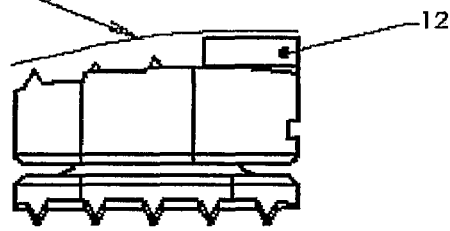
FIG. 1D is a lateral view of the intervertebral disc replacement of FIG. 1A assembled.

The operation of the articulation arrangement formed by cooperation of articulation surfaces 104 and 106 will now be understood by reference to FIGS. 1C through 5C. Turning first to FIGS. 1C and 1D, at or near the neutral position of the intervertebral disc replacement, the flattened crest 110 of protuberance 32 sits on the base of recess 30 providing load-bearing support with a given minimum intervertebral spacing.

Figures 2A, 2B:
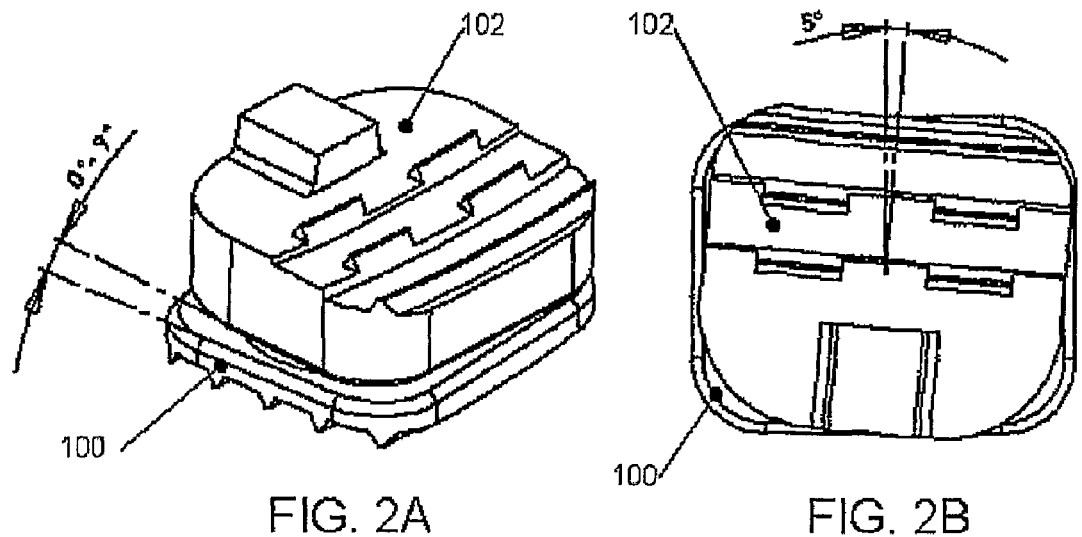
FIG. 2A is an isometric view of the intervertebral disc replacement of FIG. 1A axially rotated.
FIG. 2B is a plan view of the intervertebral disc replacement of FIG. 1A axially rotated.
Figure 2C:
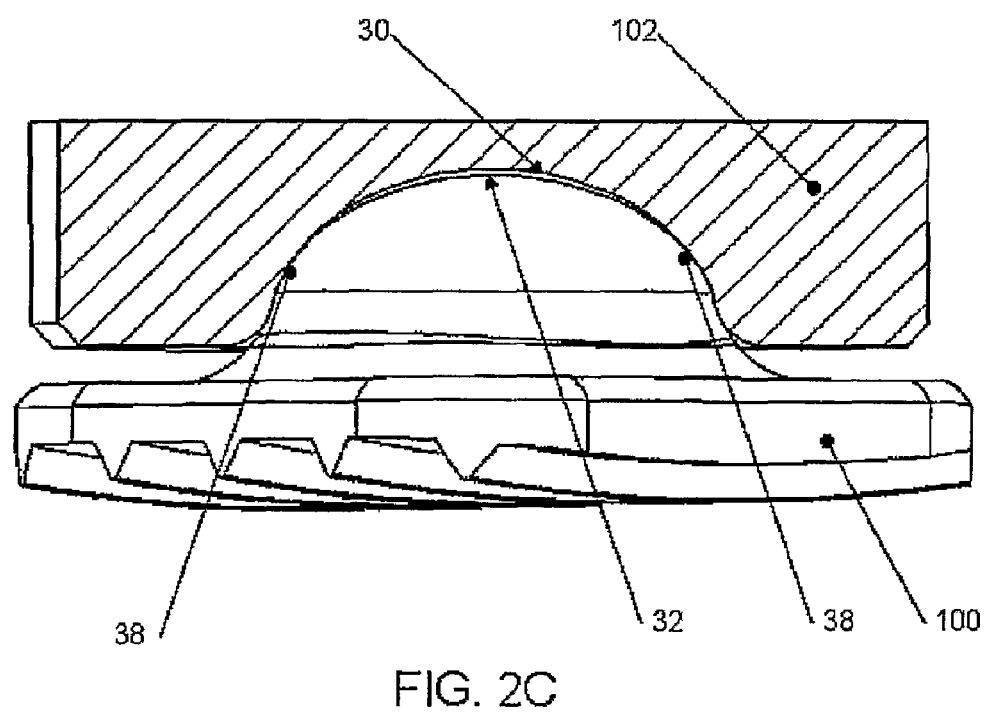
FIG. 2C is a partially cut-away view taken through the intervertebral disc replacement of FIG. 1A showing the location of contact points between the two joint members during axial rotation.
Figure 2D:
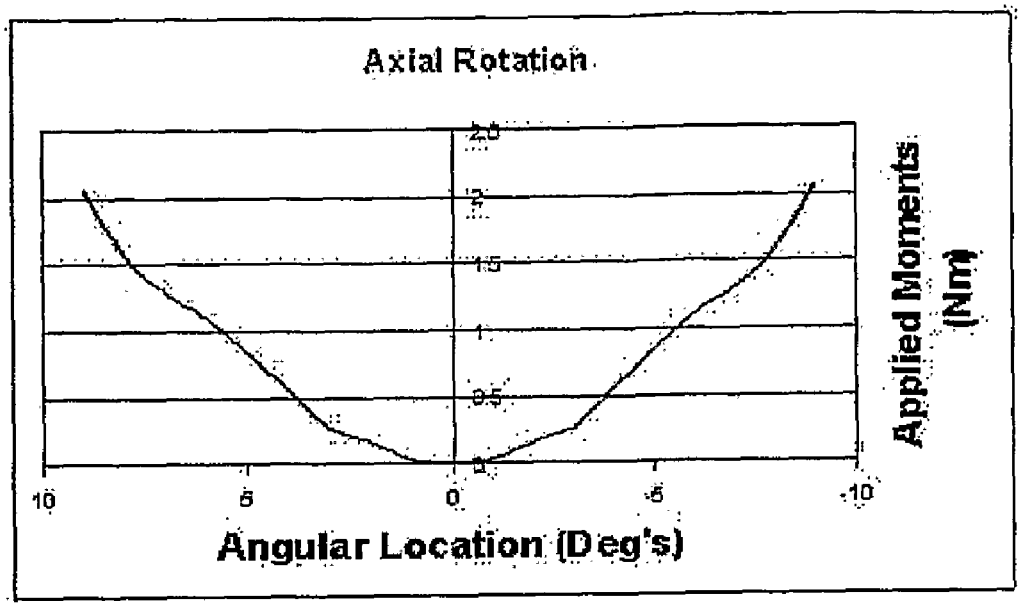
FIG. 2D is a graph showing an applied moment of axial rotation and the corresponding angular deflection of axial rotation from a neutral position for the intervertebral disc replacement of FIG. 1A under conditions of axial loading.
Figure 2E:
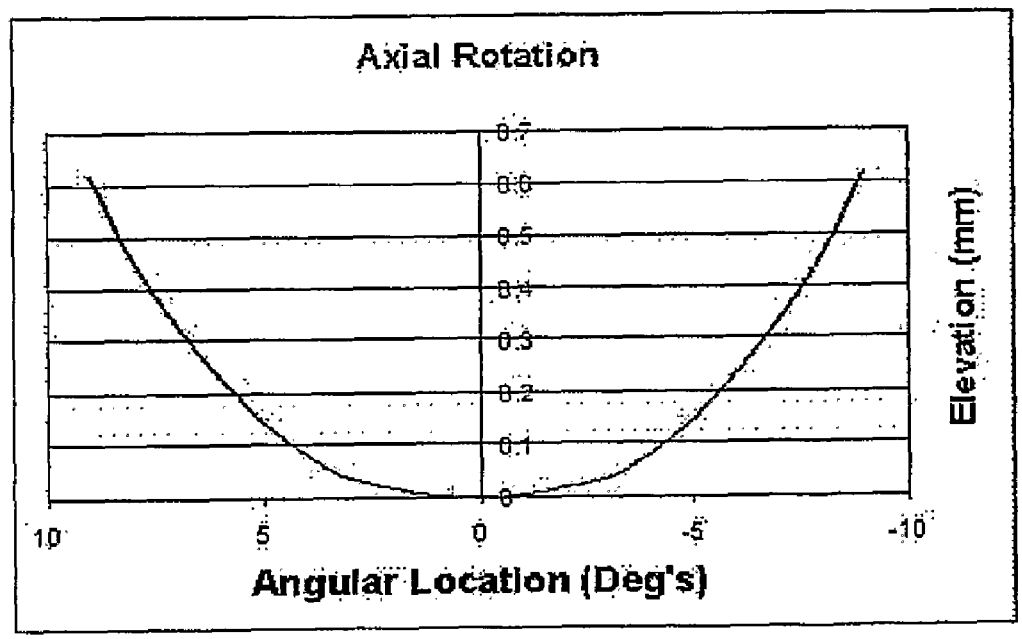
FIG. 2E is a graph showing axial elevation (increase in intervertebral spacing) as a function of angular deflection of axial rotation from a neutral position for the intervertebral disc replacement of FIG. 1A.

FIGS. 2A-2C illustrate axial rotation between members 100 and 102. As the long axes of the elliptical shapes of protuberance 32 and recess 30 become progressively out of alignment, the sloped flank surfaces of protuberance 32 and recess 30 ride up against each other, causing an increase in intervertebral spacing. During this motion, contact pressure between articulation surfaces 104 and 106 moves away from the crest of the crown region, typically being divided between two points of contact 38 as seen in the cut-away view of FIG. 2C. The applied axial turning moment corresponding to each angular deflection under axial loading of 150 N is shown in FIG. 2D, and the corresponding increase in intervertebral spacing for each angular deflection is shown in FIG. 2E. It will be noted that, as mentioned above, the applied moment increases monotonically and continuously as a function of deflection angle, while the intervertebral spacing climbs increasingly steeply (approximating to a parabola).

Figure 3A:
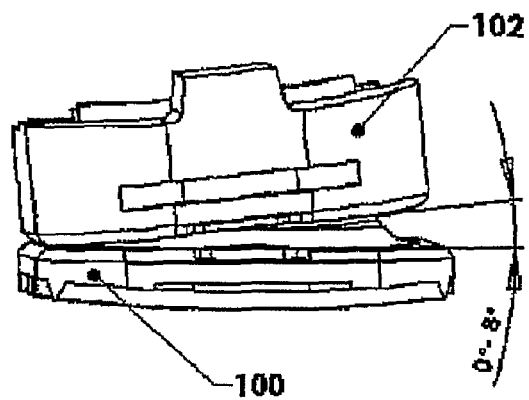
FIG. 3A is a dorsal view of the intervertebral disc replacement of FIG. 1A undergoing lateral bending.
Figure 3B:
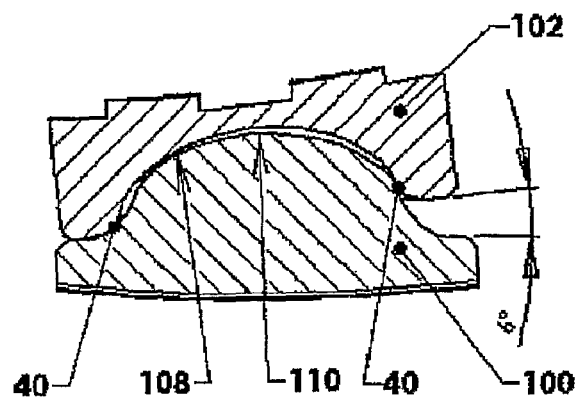
FIG. 3B is a coronal cross-sectional view of the intervertebral disc replacement of FIG. 1A undergoing lateral bending.
Figure 3C:
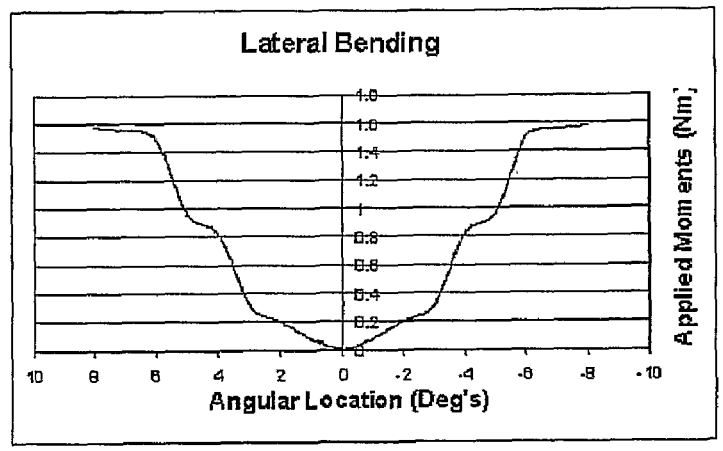
FIG. 3C is a graph showing an applied moment of lateral bending and the corresponding angular deflection of lateral bending from a neutral position for the intervertebral disc replacement of FIG. 1A under conditions of axial loading.
Figure 3D:
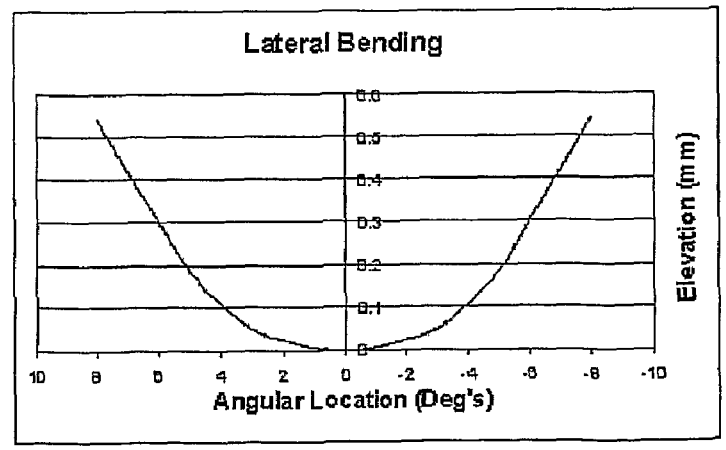
FIG. 3D is a graph showing axial elevation (increase in intervertebral spacing) as a function of angular deflection of lateral bending from a neutral position for the intervertebral disc replacement of FIG. 1.

FIGS. 3A and 3B illustrate lateral bending between members 100 and 102. As the elements tip, contact pressure is transferred from the crest of the crown portion of protuberance 32 and is split between two contact points which move progressively across the higher-curvature regions. As the motion continues, one of the contact points moves onto the concave transition region (shown as contact points 40 in FIG. 3B) and facilitates continued non-impact deflection. The applied lateral bending moment corresponding to each angular deflection under axial loading of 150 N is shown in FIG. 3C, and the corresponding increase in intervertebral spacing for each angular deflection is shown in FIG. 3D. Here too, the applied moment increases monotonically and continuously as a function of deflection angle, while the intervertebral spacing climbs increasingly steeply.

FIGS. 4A and 4B illustrate posterior extension between members 100 and 102. Here the motion is essentially similar to the lateral bending of FIGS. 3A and 3B, with the contact points 42 being shown in FIG. 4B. The applied posterior extension moment corresponding to each angular deflection under axial loading of 150 N is shown in FIG. 4C, and the corresponding increase in intervertebral spacing for each angular deflection is shown in FIG. 4D. Here again, the applied moment increases monotonically and continuously as a function of deflection angle. In this case, the intervertebral spacing remains low over a relatively large part of the range of motion near the neutral position, and then climbs increasingly steeply to provide non-impact motion attenuation towards the intended limits of the range of motion.

Parenthetically, it will be noted that acceptable results of motion attenuation have been achieved experimentally despite considerable variations in the shape of the moment vs. deflection functions. In fact, the various graphs referred to above correspond to experimental results obtained for a prototype designed by trial and error using parametrically defined articulation surfaces of the general form described above and varying the parameters in conjunction with tests for solid body overlap in basic CAD software to achieve the required profile of elevation for axial rotation. Parameters relevant to lateral bending and flexion/extension were optimized only for the surfaces of concave transition region 112 and the cooperating surfaces of convexly curved transition region 114, again by trial and error. The resulting structure was found to be highly effective in motion attenuation and self-centering properties in all directions of motion, despite considerable non-uniformities in the moment vs. deflection functions. If desired, more sophisticated CAD tools and/or numerical methods may be used to simultaneously optimize parameters for the different types of motion.

Figure 5A:
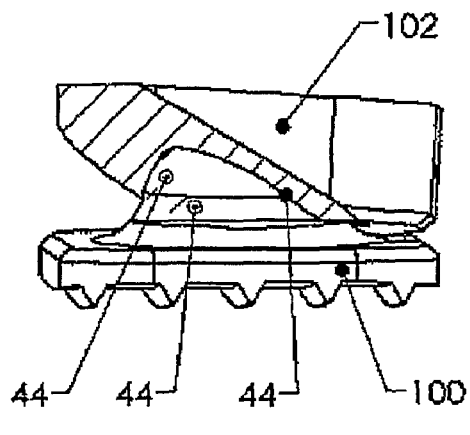
FIGS. 5A and 5B are first and second isometric partially cut-away views of the intervertebral disc replacement of FIG. 1A illustrating displaced from the neutral position by a combination of 5 degrees of flexion, 4 degrees of lateral bending and 4 degrees of axial rotation, the views illustrating the positions of three points of contact between articulation surfaces of the first and second bodies.
Figure 5B:
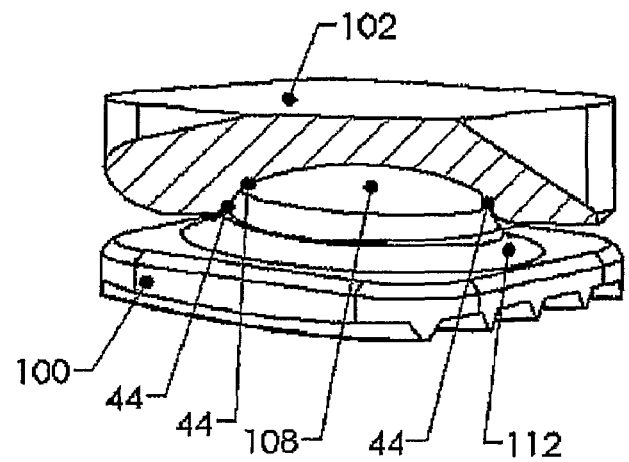
Figure 5C:
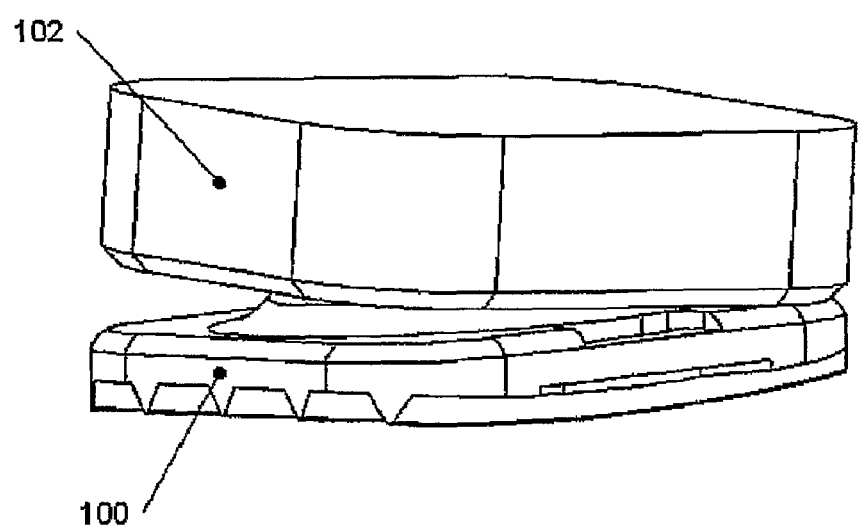
FIG. 5C is a complete isometric view of the intervertebral disc replacement of FIG. 1A showing the state of displacement of FIGS. 5A and 5B.
Figure 6A:
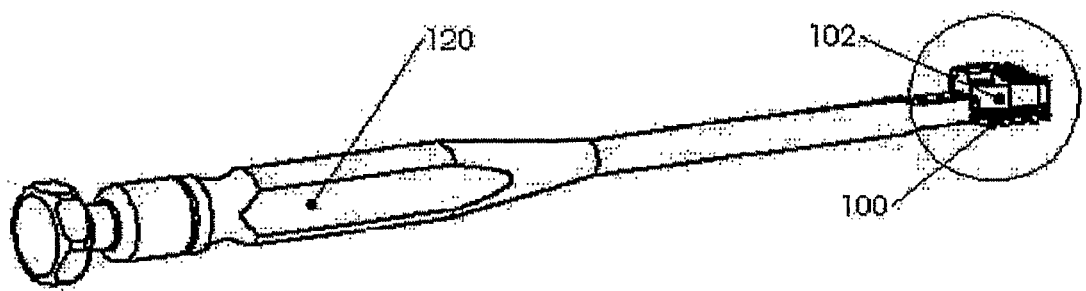
FIG. 6A is an isometric view of the intervertebral disc replacement of FIG. 1A attached to a delivery system.
Figure 6B:
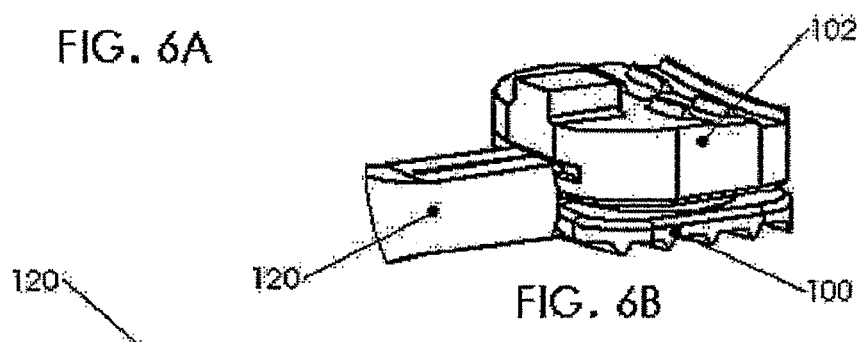
FIG. 6B is an enlarged view of the distal portion of the delivery system of FIG. 6A together with the intervertebral disc replacement of FIG. 1A.
Figure 6C:
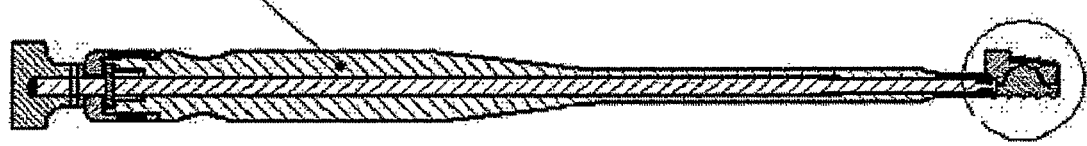
FIG. 6C is a longitudinal cross-sectional view taken through the delivery system and intervertebral disc replacement of FIG. 6A.
Figure 6D:
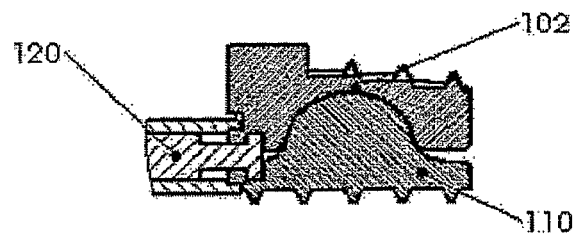
FIG. 6D is an enlarged view of the distal portion of FIG. 6C.

Referring now to FIGS. 5A-5C, as mentioned earlier, the articulation arrangements of the present invention preferably allow relative displacement of members 102 and 100 in motion corresponding to combinations of axial rotation, anterior-flexion or posterior extension, and lateral bending. By way of illustration, FIGS. 5A-5C illustrate the intervertebral disc replacement with the members displaced from the neutral position by a combination of 5 degrees of flexion, 4 degrees of lateral bending and 4 degrees of axial rotation. In general, compound motions such as this result in three points of contact, here shown as points 44 in the cut-away views of FIGS. 5A and 5B. The apparatus exhibits simultaneously non-impact motion attenuation and restoring forces in each of the planes of motion.

Turning now to the remaining features of the first embodiment of the present invention, FIGS. 1A and 1B show a preferred implementation for superior endplate contact 10 and inferior endplate contact 22, configured to achieve a reliable fixation within the upper and lower vertebral endplates, with osteointegration subsequently taking over in order to further enhance the device's bone purchasing. The basic contour of the superior endplate contact 10 preferably has a mild concavity in the latero-lateral (LL) direction 26, and general line of graduated convexity in the antero-posterior plane, represented by virtual line 28. This specific form is believed to be advantageous for mating with the relevant concavity of the superior cervical endplate in which endplate contact 10 is to be affixed. Graduated convexity 28 confers to the device about 1-1.5 mm anterior height elevation compared to its posterior aspect, thereby helping to restore the mutual positioning of the vertebrae and their interspaces, both in the intervertebral space and in the entire segmental arrangement. This formation also helps provide engagement that reduces the risk of migration in the early fixation stage. The LL concavity 26 helps to fit the general anatomic superior endplate contour of the cervical vertebrae and to avoid potential small lateral migrations in the early fixation stage of the post implantation procedure. The inferior endplate contact surface 22 is designed to present a convexity in its LL direction in order to facilitate its accommodation within the anatomical plane of the inferior cervical vertebral surface. The inferior component of the device is designed to be implanted in between the uncovertebral processes, secured against lateral migration by these bone structures. In addition to the overall contours of both endplate contact surfaces 10 and 22, these surfaces feature protruding ridges in order to enhance anchorage of the device within the vertebral endplates. The posterior anchoring ridges 14 on the superior surface 10 are latero-lateral oriented designed to be inserted within the vertebral endplate in order to resist any antero-posterior potential migration. Triangular surfaces 16 are formed at the ends and intermediate breaks in the ridges 14 and serve as surfaces resisting potential undesired lateral migration. The anterior anchoring prominence 12 is designed to be inserted within the vertebral endplate in order to enhance fixation. The entire prominence is of trapezoid configuration in order to be inserted as a wedge within the vertebral endplate. The base of prominence 12 is enlarged comparing to its upper surface in order to achieve a 'press-fit' effect that will fix the implant to achieve rapid osteo-integration.

For the lumbar vertebrae, both endplate engagement surfaces are preferably bi-convex with a pattern of fixation-enhancing projections similar to that described above. The bi-convex form is configured to "press fit" into the generally concave upper and lower lumbar vertebrae concavities, thereby helping to prevent migration and enhancing bone purchasing.

The intervertebral disc replacement of FIG. 1A is completely, or at least its majority, implanted within the volume of the intervertebral space. Consequently, its entire superior and inferior superficial circumferences (footprints), as well as, its entire volumetric contour preferably do not protrude out of the endplate cortical margins. The intervertebral space that used to contain the natural cartilaginous disc will equally accommodate the TDR. It comes into close contact with the vertebral endplate and can be implanted in single or more then one intervertebral space (including consecutive intervertebral spaces). Additionally, or as an alternative to some of the aforementioned features, contact and fixation may be enhanced by additional techniques including, but not limited to: use of screws for fixation of surfaces to the vertebral endplate; providing surfaces with micro- or nano-roughness; and employing osteoconductive or osteoinductive biocompatible materials, such as ceramics, metals or biologically active agents, on the endplate contact surface to conduct or induce bone proliferation or otherwise enhance ultimate osteo-integration.

Dimensions of the cervical implants are chosen according to the typical dimensions of the intended implant location. For cervical applications, antero-posterior (AP) dimensions are typically about 15 millimeters for both superior and inferior endplates. In the LL direction, dimensions are typically in the range of about 18-24 millimeters for the inferior surface of the inteverterbral space and about 17-22 millimeters for the superior surface of the intervertebral space. For lumbar applications, dimensions of about 25 millimeters in the AP direction and 30-38 millimeters in the LL direction are typically used.

Once the device is implanted within the intervertebral space, a desired minimum intervertebral spacing, typically in the range of 6-8 millimeters, is maintained. In certain preferred embodiments, particularly for lumbar and cervical applications, a naturally occurring amount of Lordosis (typically about 4-6 degrees) is restored. In the preferred implementation illustrated here, the presence of anterior anchoring prominence 12 and a relatively low posterior region in the second vertebral contact surface 10 together give a sloped overall vertebral contact profile, thereby giving the entire intervertebral disc replacement an effective wedge-shaped profile to provide the aforementioned Lordosis.

Preferred ranges of motion (ROM) over which the aforementioned mechanical properties of the apparatus of the present invention hold true are typically about 9 degrees of axial rotation in either direction from the neutral position, and about 8 degrees in each direction of lateral bending, anterior flexion and posterior extension. These values may be somewhat diminished during coupled motion in more than one direction, as is true also in a natural joint. However, ranges of axial rotation and lateral bending in the range up to about 4 or 5 degrees are usually more than sufficient to accommodate the clinically relevant ranges of motion. Actual ranges of motion for each individual patient are determined by factors such as the state of the facet joints and other surrounding tissues. Even where smaller ranges of motion are available, the present invention still provides functions of non-impact motion attenuation and restoring forces within that range of motion.

Turning now to the insertion of the intervertebral disc replacement of the present invention, FIGS. 1A-1C show superior and inferior holder slots 18 and 20 located on the anterior edge of the implant. These slots are engaged by a delivery device 120 (FIGS. 6A-6D) configured to hold the apparatus and retain the first and second members in their neutral position during insertion into the intervertebral space. Further details of the delivery device and surgical techniques will be clear to one ordinarily skilled in the art, and will not be presented here.

First and second members 100 and 102 may be formed from any durable biocompatible material. Preferably, the first and second members are substantially rigid bodies. Preferred materials include, but are not limited to, metallic materials, ceramic materials and polymer materials. Specific preferred examples for metallic materials suitable for implementing the present invention include, but are not limited to, stainless steel, titanium, titanium alloys such as titanium-molybdenum-zirconium-iron (TMZF), and cobalt-chrome alloys such as cobalt-chromium-molybdenum. Optionally, the articulation surfaces of the elements may have surface treatments or coatings to improve resistance to wear, to reduce friction or to provide any other desired mechanical or medical properties. By way of non-limiting examples, suitable coating materials useful for reducing friction or wear include, but are not limited to, CrN (chrome nitride) and other chromium based coating, TiN (titanium nitride), diamond, and diamond-like materials.

Turning now to FIGS. 7A-7F, these illustrate an alternative approach to implementing the principles of the present invention. The apparatus shown here is analogous in function to the embodiment of FIG. 1A, providing non-impact gradual motion attenuation and restoring forces in all directions of motion through increasing the intervertebral spacing. This implementation differs from that of FIG. 1A primarily in the geometrical structure. In this case, both articulation surfaces 104 and 106 feature a plurality of recesses 130, 132, and the articulating arrangement further includes a corresponding plurality of bearing elements 64, each entrapped between a facing pair of the recesses 130 and 132. In the particularly preferred implementation shown here, bearing elements 64 are implemented as ball bearings, thereby providing a particularly low-friction rolling interface between the upper and lower members.

In this embodiment, the increase in intervertebral spacing is achieved by offsetting of the positions of recesses 130 relative to recesses 132. In the particularly preferred implementation illustrated here, recesses 130 and 132 are all partial spherical recesses of radius of curvature greater than ball bearings 64, with recesses 130 spread further apart than recesses 132. As a result, in the neutral position illustrated in FIGS. 7C and 7E, ball bearings 64 sit off-center with respect to each recess, contacting opposing faces across a diameter of each ball as shown at points 62. During motion, the relative offset between the pairs of facing recesses 130, 132 changes. FIG. 7D illustrates the resulting position and new contact points 58 for axial rotation of 5 degrees. FIG. 7F illustrates similarly for lateral bending of 4 degrees. In each case, at least some of ball bearings 64 reach a position where contact with the recesses occurs at a point higher on the walls of the recesses 130 and 132, thereby causing the required increase in intervertebral spacing.

It should be noted that the number of recesses and ball bearings in this embodiment may vary. Typically, at least three bearings and corresponding pairs of recesses are used in order to provide stability. Larger numbers of bearings are possible, but may overly limit the dimensions of each bearing and hence the range of motion available. The four-ball implementation illustrated here is believed to be particularly advantageous due to the symmetry of range of motion in along the primary axes. The layout of the recesses in this case may be square or rectangular, with square symmetry preferred as offering a symmetrical range of motion in lateral bending and flexion-extension. The implementation shown here with sides of the square parallel to the primary axes of lateral bending and flexion-extension is particularly preferred, although a layout with diagonals parallel to these axes is also possible.

While the partial spherical recesses described here are believed to be particularly advantageous, it will be appreciated that recesses 130 and 132 may be implemented in other forms to achieve various different profiles of motion, including but not limited to a partial ellipsoid recess or a partial asymmetric "egg-shaped" recess. The recesses are preferably, although not necessarily, related by rotation through 180 degrees about the center of the ball bearing.

Figure 7A:
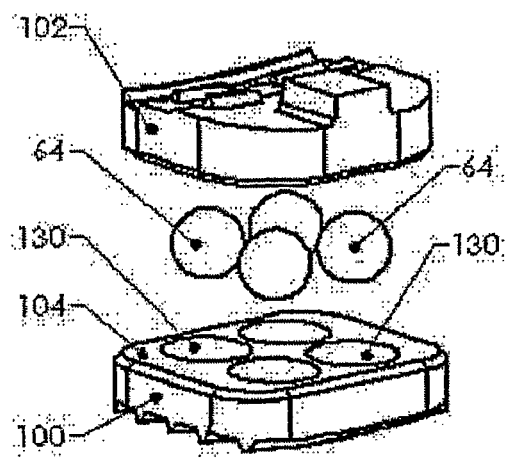
FIG. 7A is an isometric view of an alternative embodiment of an intervertebral disc replacement, constructed and operative according to the teachings of the present invention, showing first and second members separated and a number of additional ball bearings therebetween.
Figure 7B:
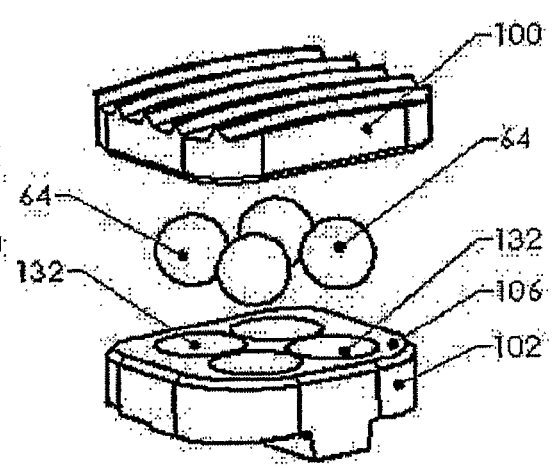
FIG. 7B is an inverted isometric view of the intervertebral disc replacement of FIG. 7A.
Figure 7C:
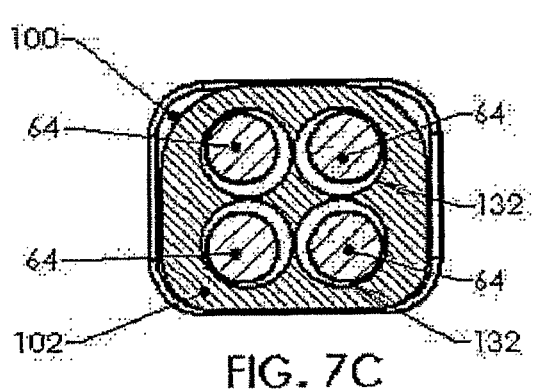
FIG. 7C is an axial cross-sectional view taken through the assembled intervertebral disc replacement of FIG. 7A in a neutral position.
Figure 7D:
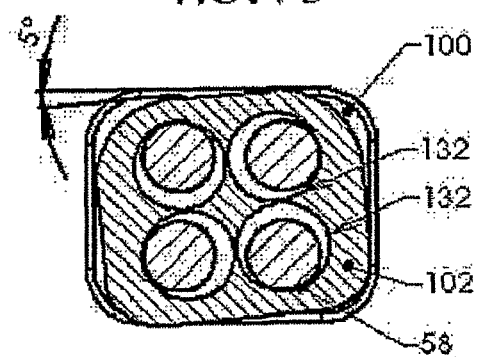
FIG. 7D is an axial cross-sectional view taken through the assembled intervertebral disc replacement of FIG. 7A undergoing axial rotation.
Figure 7E:
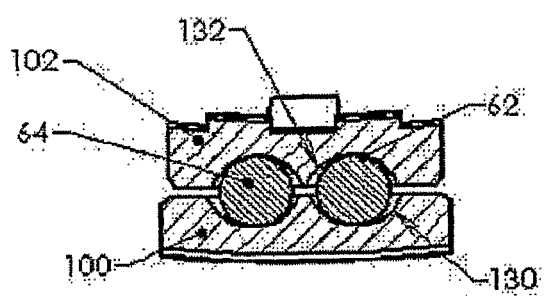
FIG. 7E is a coronal cross-sectional view taken through the assembled intervertebral disc replacement of FIG. 7A in a neutral position.
Figure 7F:
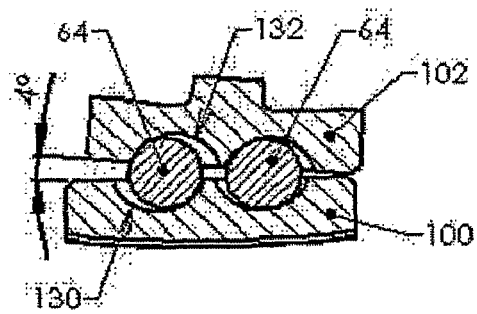
FIG. 7F is a coronal cross-sectional view taken through the assembled intervertebral disc replacement of FIG. 7A undergoing lateral bending.
Figure 7G:
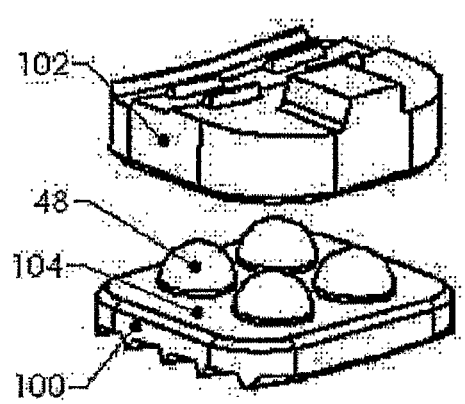
FIG. 7G is a disassembled isometric view of a variant implementation of the intervertebral disc replacement of FIG. 7A in which the ball bearings are replaced by rounded projections projecting from one of the members.
Figure 7H:
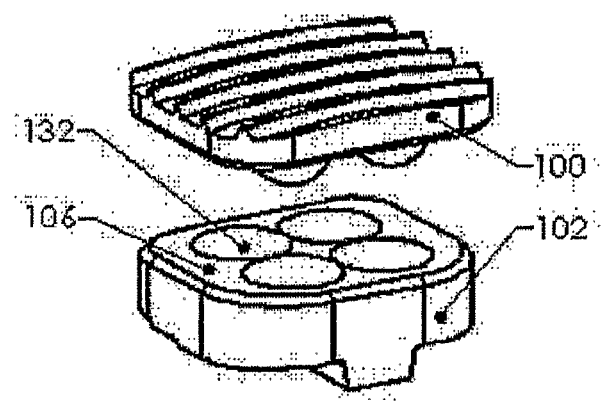
FIG. 7H is an inverted isometric view of the intervertebral disc replacement of FIG. 7G.
Figure 7I:
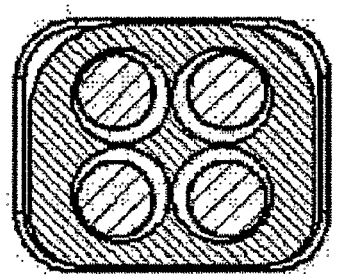
FIG. 7I is an axial cross-sectional view taken through the assembled intervertebral disc replacement of FIG. 7G in a neutral position.
Figure 7J:
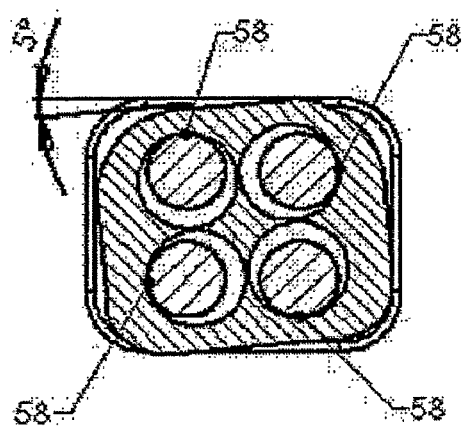
FIG. 7J is an axial cross-sectional view taken through the assembled intervertebral disc replacement of FIG. 7G undergoing axial rotation.
Figure 7K:
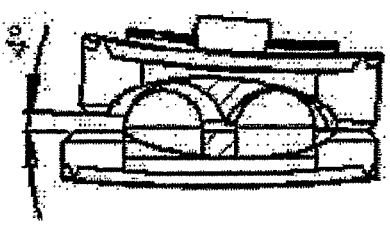
FIG. 7K is a partly cut-away dorsal view of the assembled intervertebral disc replacement of FIG. 7G undergoing lateral bending.
Figure 8A:
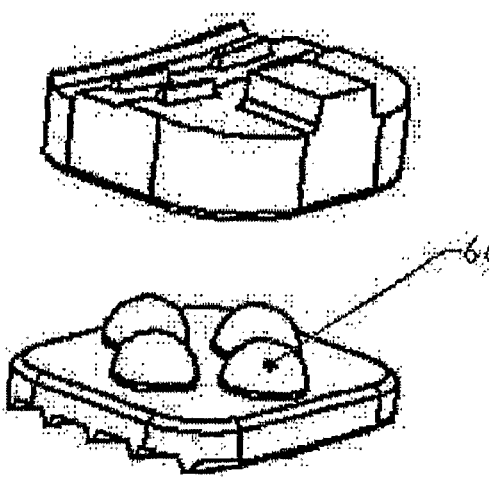
FIG. 8A is an isometric view of a further alternative embodiment of an intervertebral disc replacement, constructed and operative according to the teachings of the present invention, showing first and second members separated.
Figure 8B:
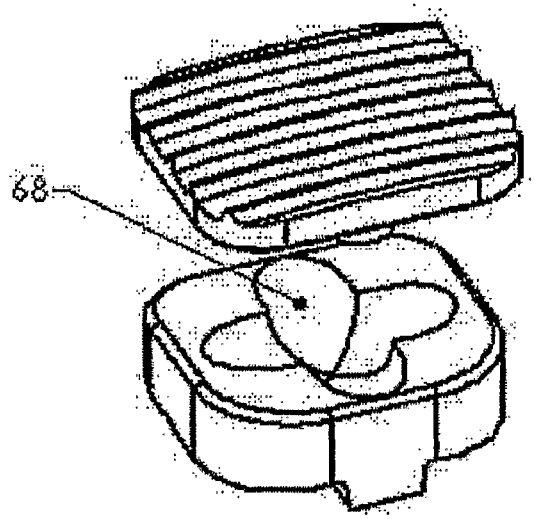
FIG. 8B is an inverted isometric view of the intervertebral disc replacement of FIG. 8A.
Figure 8C:
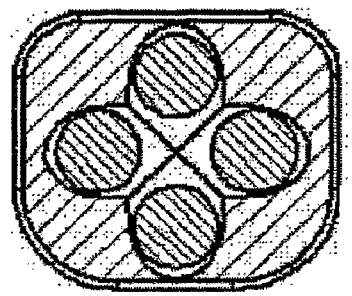
FIG. 8C is an axial cross-sectional view taken through the intervertebral disc replacement of FIG. 8A.
Figure 8D:
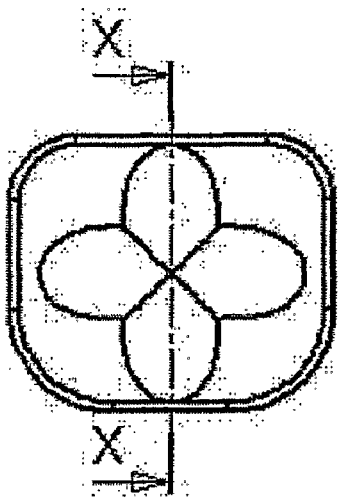
FIG. 8D is a plan view of the articulation surface of the upper member of the intervertebral disc replacement of FIG. 8A.
Figure 8E:
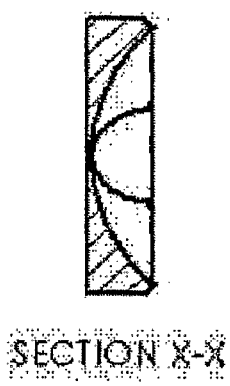
FIG. 8E is a cross-sectional view taken in a sagittal plane indicated as line X-X in FIG. 8D.
Figure 8F:
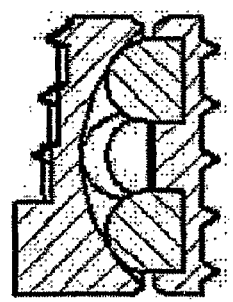
FIG. 8F is a sagittal cross-sectional view taken through the assembled intervertebral disc replacement of FIG. 8A.

Turning now to FIGS. 7G-7K, these illustrate a variant of the embodiment of FIG. 7A in which the second member 102 is unchanged, featuring recesses 132, while ball bearings 64 and recesses 130 are replaced by partially-spherical projections 48 integrally formed with first member 100. Operation of this variant is similar to that of FIGS. 7A-7F, although the motion is here a sliding contact rather than rolling, and the range of motion for a give size of recesses 132 is reduced. Clearly, the various design parameters may be varied to achieve a desired range of motion.

In all other respects, the structure and operation of these implementations may be fully understood by analogy with the embodiment of FIGS. 1A-6D described above.

Turning now to FIGS. 8A-8F, these show a further implementation of the present invention conceptually similar to that of FIGS. 7G-7K. As mentioned, the form of the recesses in second articulation surface 106 is not limited to the partial spherical recesses described above. In fact, it will be noted that the outward-facing regions of recesses 132 closest to the axial axis of the articulation arrangement do not normally contact projections 48 at all during operation. It is therefore possible to vary the shape of the recesses and, as shown here, combine the recesses into a single suitably shaped recess 68.

It follows that the only portions of recess 68 for which the shape is critical are the portions near the ends of the X-shape where the projections, here denoted 66, make contact. Clearly, these contact regions may be partial spheres, partial ellipses or any other form chosen to provide the desired dynamics.

This implementation also differs from that of FIGS. 7G-7K in that the projections 48 and corresponding recess 68 are deployed in diagonal relation at 45 degrees to the layout of FIGS. 7G-7K. In all other respects, the structure and operation of this implementation may be fully understood by analogy with the embodiments described above.

Figures 9A, 9B:
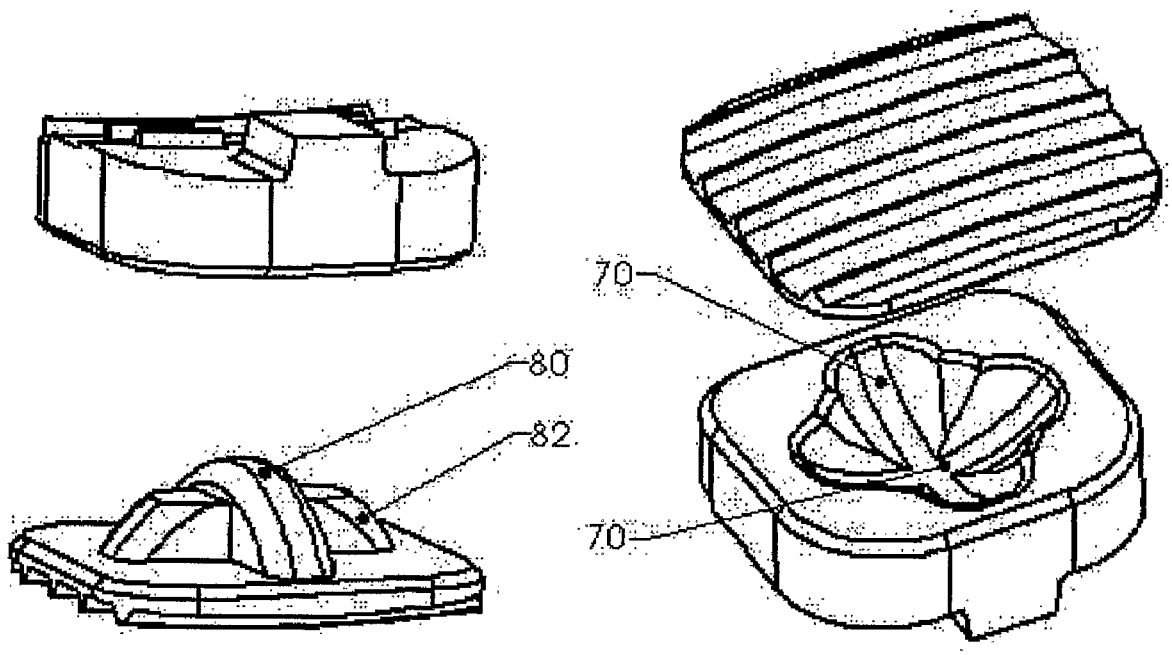
FIG. 9A is an isometric view of another embodiment of an intervertebral disc replacement, constructed and operative according to the teachings of the present invention, showing first and second members separated.
FIG. 9B is an inverted isometric view of the intervertebral disc replacement of FIG. 9A.
Figure 9C:
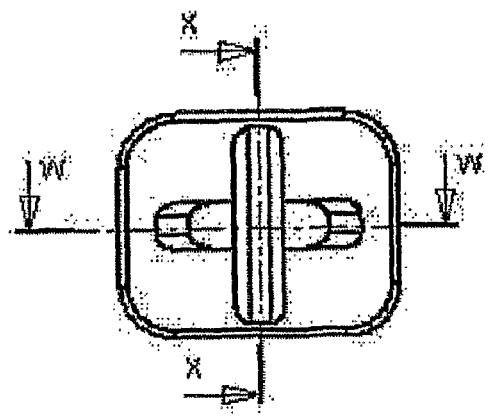
FIG. 9C is a plan view of the articulation surface of the lower member of the intervertebral disc replacement of FIG. 9A.
Figure 9D:
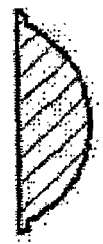
FIGS. 9D and 9E are cross-sectional views taken along the lines X-X and W-W, respectively, in FIG. 9C.
Figure 9E:
Figure 9F:
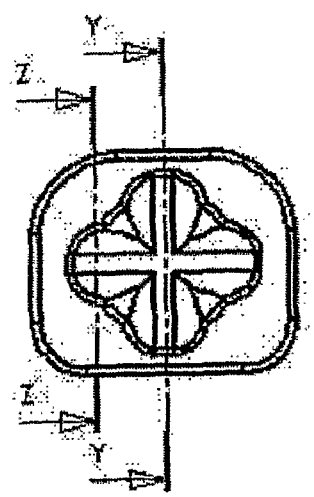
FIG. 9F is a plan view of the articulation surface of the upper member of the intervertebral disc replacement of FIG. 9A.
Figure 9G:
FIGS. 9G and 9H are cross-sectional views taken along the lines Z-Z and Y-Y, respectively, in FIG. 9F.
Figure 9H:

Turning now to FIGS. 9A-9H, these illustrate an alternative embodiment having a single protuberance shaped with two perpendicular shaped ridges 80 and 82, and a cooperating single shaped recess 70. In this case, the primary outer abutment surfaces of the ridges 80 and 82 are substantially circular, as seen in FIGS. 9D and 9E, as if part of a conventional ball-and-socket joint. In the case of ridge 82, part of the circular profile not critical to the abutment functions is cut away to facilitate manufacture. The desired increase in intervertebral spacing is here achieved by suitable shaping of the cross-section of ridges 80 and 82, as well as the cooperating flank portions of channels formed within recess 70, as best seen in FIGS. 9F-9H. Thus, in flexion-extension, it is primarily the side-to-side ridge 82 interacting with adjacent surfaces of recess 70 which is responsible for the intervertebral spacing increase while, during lateral bending, it is front-to-back ridge 80 which causes the elevation. In axial rotation, three or four contact points typically contribute to the increase in intervertebral spacing.

Figure 10A:
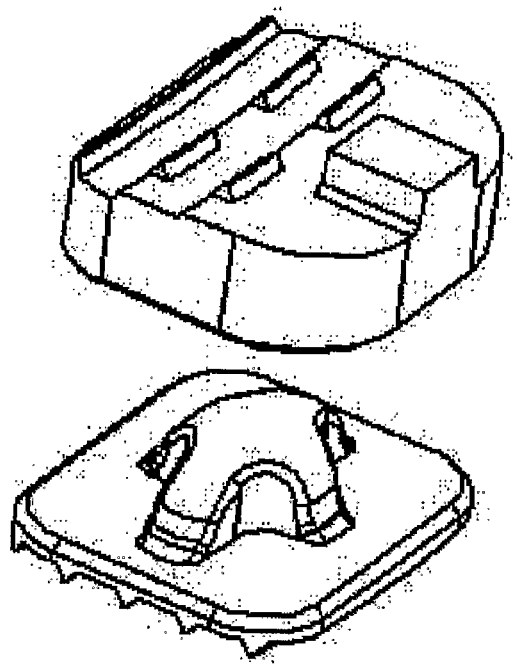
FIG. 10A is an isometric view a further embodiment of an intervertebral disc replacement, constructed and operative according to the teachings of the present invention, showing first and second members separated.
Figure 10B:
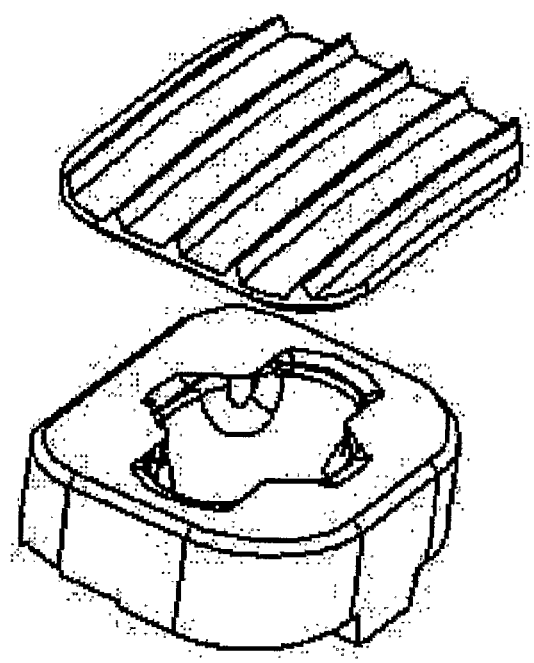
FIG. 10B is an inverted isometric view of the intervertebral disc replacement of FIG. 10A.

Turning finally to FIGS. 10A and 10B, this shows an embodiment which is conceptually a hybrid between the embodiments of FIGS. 1A and 9A. Specifically, this embodiment has an overall elliptical geometry substantially as described above with reference to FIG. 1A. Additionally, the protuberance in this case also includes a plurality of recessed flank regions, and the cooperating recess includes a corresponding plurality of ridge regions, giving additional contact surfaces similar to those of FIG. 9A. This configuration provides a larger number of design parameters which may be adjusted in the event that it is desired to optimize the intervertebral spacing profile for all directions of motion simultaneously.

It will be appreciated that the above descriptions are intended only to serve as examples, and that many other embodiments are possible within the scope of the present invention as defined in the appended claims.

What is claimed is:

1. An apparatus for replacing at least a portion of an intervertebral disc in a spinal column between endplates of a first vertebral body and a second vertebral body of a spinal column, the apparatus comprising:
    (a) a first member having a first vertebral contact surface for engagement with the first vertebral body endplate, and having a first articulation surface; and
    (b) a second member having a second vertebral contact surface for engagement with the second vertebral body endplate, and having a second articulation surface,
wherein an intervertebral spacing is defined as the axial component of a line extending between a centroid of said first vertebral contact surface and a centroid of said second vertebral contact surface,
and wherein said first articulation surface and said second articulation surface form at least part of an articulation arrangement configured such that, when loaded with compressive axial force:
    (i) said first and second vertebral contact surfaces are supported against the compressive force to ensure a predefined minimum intervertebral spacing;
    (ii) said second member is displaceable relative to said first member in motion corresponding to axial rotation, anterior-flexion and posterior extension, and lateral bending, each of said motions having a corresponding range of motion; and
    (iii) said intervertebral spacing increases as a smooth function of angular displacement from a neutral position over at least part of said range of motion in each direction for each of said axial rotation, anterior-flexion and posterior extension, and lateral flexion, thereby providing non-impact motion attenuation.

2. The apparatus of claim 1, wherein said articulation arrangement is configured such that a first derivative of intervertebral spacing as a function of angular displacement from a neutral position increases substantially monotonically with respect to said angular displacement from said neutral position over a majority of said range of motion for motion in each direction for each of said axial rotation, anterior-flexion and posterior extension, and lateral flexion.

3. The apparatus of claim 1, wherein said articulation arrangement is configured such that said second member is displaceable relative to said first member in motion corresponding to combinations of axial rotation, anterior flexion or posterior extension, and lateral bending.

4. The apparatus of claim 1, wherein said articulation arrangement is configured such that the apparatus is self-centering under axial loading so as to tend to return substantially to a predefined neutral position.

5. The apparatus of claim 1, wherein said first member and said second member are rigid bodies.

6. The apparatus of claim 1, wherein said first member and said second member are formed primarily from metallic material.

7. The apparatus of claim 1, wherein said first member and said second member are formed primarily from ceramic material.

8. The apparatus of claim 1, wherein said first articulation surface and said second articulation surface are deployed in direct contact to provide said articulation arrangement.

9. The apparatus of claim 1, wherein said first articulation surface features a protuberance and said second articulation surface features a cooperating recess, wherein said protuberance is shaped such that, in sagittal cross-section, an external shape of said protuberance features:
  (a) a convexly curved crown region having varying curvature with a local minimum of curvature at a crest of said crown region; and
  (b) a concavely curved transition region at the base of said protuberance.

10. The apparatus of claim 9, wherein said protuberance is further shaped such that, in coronal cross-section, an external shape of said protuberance features:
  (a) a convexly curved crown region having varying curvature with a local minimum of curvature at a crest of said crown region; and
  (b) a concavely curved transition region at the base of said protuberance.

11. The apparatus of claim 10, wherein said protuberance is further shaped such that a width of said protuberance in said coronal cross-section is greater than a width of said protuberance in said sagittal cross-section.

12. The apparatus of claim 10, wherein said protuberance is further shaped such that, in axial cross-section, an external shape of said protuberance is substantially elliptical.

13. The apparatus of claim 12, wherein said cooperating recess is formed substantially as an elliptical concavity with a convexly curved transition region connecting to a surrounding area of said second articulation surface.

14. The apparatus of claim 10, wherein said protuberance exhibits a plurality of recessed flank regions, and wherein said cooperating recess includes a corresponding plurality of ridge regions.

15. The apparatus of claim 1, wherein said first articulation surface features a protuberance including a plurality of ridges, and wherein said second, articulation surface features a cooperating recess including a plurality of channels for receiving said ridges, wherein said ridges interact with adjacent surfaces of said channels to generate said increase in intervertebral spacing.

16. The apparatus of claim 1, wherein said first articulation surface features a plurality of protuberances and said second articulation surface features cooperating recessed features.

17. The apparatus of claim 1, wherein said first articulation surface features a plurality of recesses and said second articulation surface features a corresponding plurality of recesses, said articulating arrangement further including a corresponding plurality of bearing elements, each of said bearing elements being entrapped between a facing pair of said recesses of said first and second articulation surfaces.

18. The apparatus of claim 17, wherein said bearing elements are implemented as ball bearings.

19. The apparatus of claim 18, wherein said plurality of recesses of said first and second articulation surfaces are implemented as partial spherical recesses of radius of curvature greater than said ball bearings, locations of said recesses of said first articulation surface being offset relative to locations of said recesses of said second articulation surface.

20. The apparatus of claim 19, wherein said articulation arrangement is implemented with four of said ball bearings and four of said recesses in each of said first and second articulation surfaces.

* * * * *